US005868693A

United States Patent [19]
Duback et al.

[11] Patent Number: 5,868,693
[45] Date of Patent: Feb. 9, 1999

[54] CUSTOM-FITTED ATHLETIC ANKLE BRACE

[75] Inventors: Jeffrey E. Duback, Davidson; Carole B. Floyd, Stanley; Mark G. Friday, Dallas, all of N.C.

[73] Assignee: Parker Medical Associates Limited Partnership, Charlotte, N.C.

[21] Appl. No.: 926,924

[22] Filed: Sep. 10, 1997

[51] Int. Cl.⁶ .................................................. A61F 5/00
[52] U.S. Cl. ...................... 602/27; 602/6; 602/7
[58] Field of Search .................... 602/27–29, 65, 602/6–8; 128/882

[56] References Cited

U.S. PATENT DOCUMENTS

| 346,606 | 8/1886 | Pugsley | 602/65 |
|---|---|---|---|
| 398,892 | 3/1889 | Golden | 602/65 |
| 487,492 | 12/1892 | Pugsley | 602/65 |
| 674,066 | 5/1901 | Mitchell | 602/65 |
| 1,084,197 | 1/1914 | Collis | 602/65 |
| 1,116,133 | 11/1914 | Schusheim | 602/65 |
| 1,397,095 | 11/1921 | Hamilton | 602/65 |
| 1,465,233 | 8/1923 | Posner | 602/65 |
| 3,298,365 | 1/1967 | Lewis | 602/27 |
| 3,584,622 | 6/1971 | Domenico | 602/65 |
| 4,411,262 | 10/1983 | Von Bonin et al. | 428/266 X |
| 4,630,600 | 12/1986 | Spencer et al. | 602/27 |
| 4,638,794 | 1/1987 | Grisar | 602/27 |
| 4,821,743 | 4/1989 | Wetz . | |
| 5,000,195 | 3/1991 | Neal | 602/27 |
| 5,056,509 | 10/1991 | Swearington . | |
| 5,113,877 | 5/1992 | Johnson, Jr. et al. . | |
| 5,259,834 | 11/1993 | Wittmeyer | 602/27 X |
| 5,330,419 | 7/1994 | Toronto et al. . | |
| 5,389,065 | 2/1995 | Johnson, Jr. . | |
| 5,393,303 | 2/1995 | Shiono . | |
| 5,430,960 | 7/1995 | Richardson . | |
| 5,435,009 | 7/1995 | Schild et al. | 602/27 X |
| 5,449,005 | 9/1995 | Echols | 602/27 X |
| 5,454,780 | 10/1995 | Duback et al. | 602/27 X |
| 5,544,663 | 8/1996 | Duback | 602/8 X |
| 5,637,077 | 6/1997 | Parker | 602/27 X |
| 5,676,641 | 10/1997 | Arensdorf et al. | 602/27 |
| 5,720,715 | 2/1998 | Eriksson | 602/27 X |

Primary Examiner—Linda C. M. Dvorak
Attorney, Agent, or Firm—Adams Law Firm, P.A.

[57] ABSTRACT

An athletic ankle brace is custom-formed to the shape of a wearer's ankle. The ankle brace includes a hardenable brace panel adapted for being molded while flexible to the medial and lateral aspects of the lower leg and ankle of the wearer. Upon hardening, the molded brace panel provides a rigid custom fit for restricting inversion and eversion of the foot during wear. The brace panel defines an integrally-formed hardenable posterior heel tongue adapted for being molded while flexible to the heel of the wearer and extending under the heel to further support the ankle upon hardening.

15 Claims, 9 Drawing Sheets

CUSTOM-FITTED ATHLETIC ANKLE BRACE

TECHNICAL FIELD AND BACKGROUND OF THE INVENTION

This invention relates to a custom-fitted athletic ankle brace. The invention has particular application as an athletic support device for protecting the ankle and Achilles tendon from injury or increased injury during sports activities. The invention readily conforms to the ankle to provide a custom fit, and is relatively thin and lightweight. Moreover, the invention is quickly and easily custom molded to suit the particular wearer.

Athletes and other active persons commonly suffer slight to moderate sprains of the anterior talofibular ligament at the interior margin of the lateral malleolus. In such cases, it is essential to brace the ankle in such a way as to substantially stabilize the ankle against eversion and inversion while permitting dorsiflexion and planoflexion necessary for participation in sports, normal waking, and other exercise.

The present invention takes advantage of polymer chemistry to permit quick and easy molding of a brace to the ankle. Shock attenuation is increased since the custom fit spreads contact between the brace and the ankle over a wider surface area. The invention permits application of an ankle brace to a body part in such a way as to achieve a true custom fit. The moisture curable resin system used results in a rigid ankle brace which holds the shape of the molded brace to a high degree. No heat is required, and a source of water is the only additional material necessary to achieve curing. Atmospheric moisture alone will cure the brace into its hardened position in a relatively short period of time, but in practice the resin in or on the brace will typically be activated by dipping in water.

SUMMARY OF THE INVENTION

Therefore, it is an object of the invention to provide an ankle brace which can be molded to an ankle to stabilize the ankle against eversion and inversion while permitting dorsiflexion and planoflexion necessary for participation in sports, normal walking, and other exercise.

It is another object of the invention to provide an ankle brace which is particularly applicable for use as an athletic support device.

It is another object of the invention to provide an ankle brace which can be custom-fitted to a particular wearer.

It is another object of the invention to provide an ankle brace which is comfortable against the Achilles tendon of the wearer.

It is another object of the invention to provide an ankle brace which hardens in the presence of moisture to form a rigid but very lightweight brace.

It is another object of the invention to provide an ankle brace which can be worn without the need for the brace to be held into place by straps or belts.

It is another object of the invention to provide an ankle brace which can be worn inside a shoe.

It is another object of the invention to provide a ankle brace which is stored in a moisture-proof foil until ready for application to the ankle.

It is another object of the invention to provide an ankle brace which is formed of a thermosetting material.

These and other objects of the present invention are achieved in the preferred embodiments disclosed below by providing an ankle brace for being custom-formed to the shape of a wearer's ankle. The ankle brace includes a brace panel adapted for being formed to the medial and lateral aspects of the lower leg and ankle of the wearer. The brace panel is permanently molded to provide a rigid custom fit for restricting inversion and eversion of the foot during wear. The brace panel defines an integrally-formed posterior heel tongue adapted for being formed to the heel of the wearer and permanently molded to further support the ankle upon hardening.

According to one preferred embodiment of the invention, the brace panel defines a flexible Achilles zone adapted for extending along a vertical dimension of the Achilles tendon of the wearer to allow flexing of the Achilles tendon upon dorsiflexion and planoflexion of the foot.

According to another preferred embodiment of the invention, the brace panel includes a plurality of fiberglass fabric layers impregnated with a moisture-curable resin which hardens when exposed to moisture.

According to yet another preferred embodiment of the invention, the Achilles zone of the brace panel is completely devoid of fiberglass fabric.

According to yet another preferred embodiment of the invention, fastener means are provided for securing the brace panel in position around the lower leg and ankle of the wearer.

According to yet another preferred embodiment of the invention, the fastener means is a zipper extending from a proximal end of the ankle brace to a distal end of the ankle brace.

According to yet another preferred embodiment of the invention, the fastener means includes complementary hook and loop straps.

According to yet another preferred embodiment of the invention, the fastener means includes cooperating laces.

According to yet another preferred embodiment of the invention, at least one longitudinal hinge line divides the brace panel into adjacent brace segments flexibly attached together along the hinge line, and cooperating to allow ready insertion and removal of the foot into and from the ankle brace.

According to yet another preferred embodiment of the invention, the hinge line includes sewing stitches.

According to yet another preferred embodiment of the invention, a cushioned anterior tongue is provided for residing adjacent to a front portion of the lower leg and ankle.

According to yet another preferred embodiment of the invention, the brace panel includes a single layer of fiberglass fabric impregnated with a moisture-curable resin which hardens when exposed to moisture.

According to yet another preferred embodiment of the invention, the brace panel includes an inner cushioning layer for residing next to the skin.

According to yet another preferred embodiment of the invention, the inner cushioning layer includes polypropylene felt.

According to yet another preferred embodiment of the invention, the brace panel includes an outer layer formed of polyester netting.

According to yet another preferred embodiment of the invention, at least one pressure-relief ankle pad is attached to an inner surface of the brace panel and adapted to reside against an ankle bone of the wearer.

In another embodiment, the ankle brace includes a brace panel adapted for being formed to the medial and lateral aspects of the lower leg and ankle of the wearer. The brace panel is permanently molded to provide a rigid custom fit for restricting inversion and eversion of the foot during wear. The brace panel defines a flexible Achilles zone adapted for extending along a vertical dimension of the Achilles tendon of the wearer to allow flexing of the Achilles tendon upon dorsiflexion and planoflexion of the foot.

In yet another embodiment, the ankle brace includes a brace panel adapted for being formed to the medial and lateral aspects of the lower leg and ankle of the wearer. The brace panel is permanently molded to provide a rigid custom fit for restricting inversion and eversion of the foot during wear. At least one longitudinal hinge line divides the brace panel into adjacent brace segments flexibly attached together along the hinge line, and cooperating to allow ready insertion and removal of the foot into and from the ankle brace.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

Figure 1:
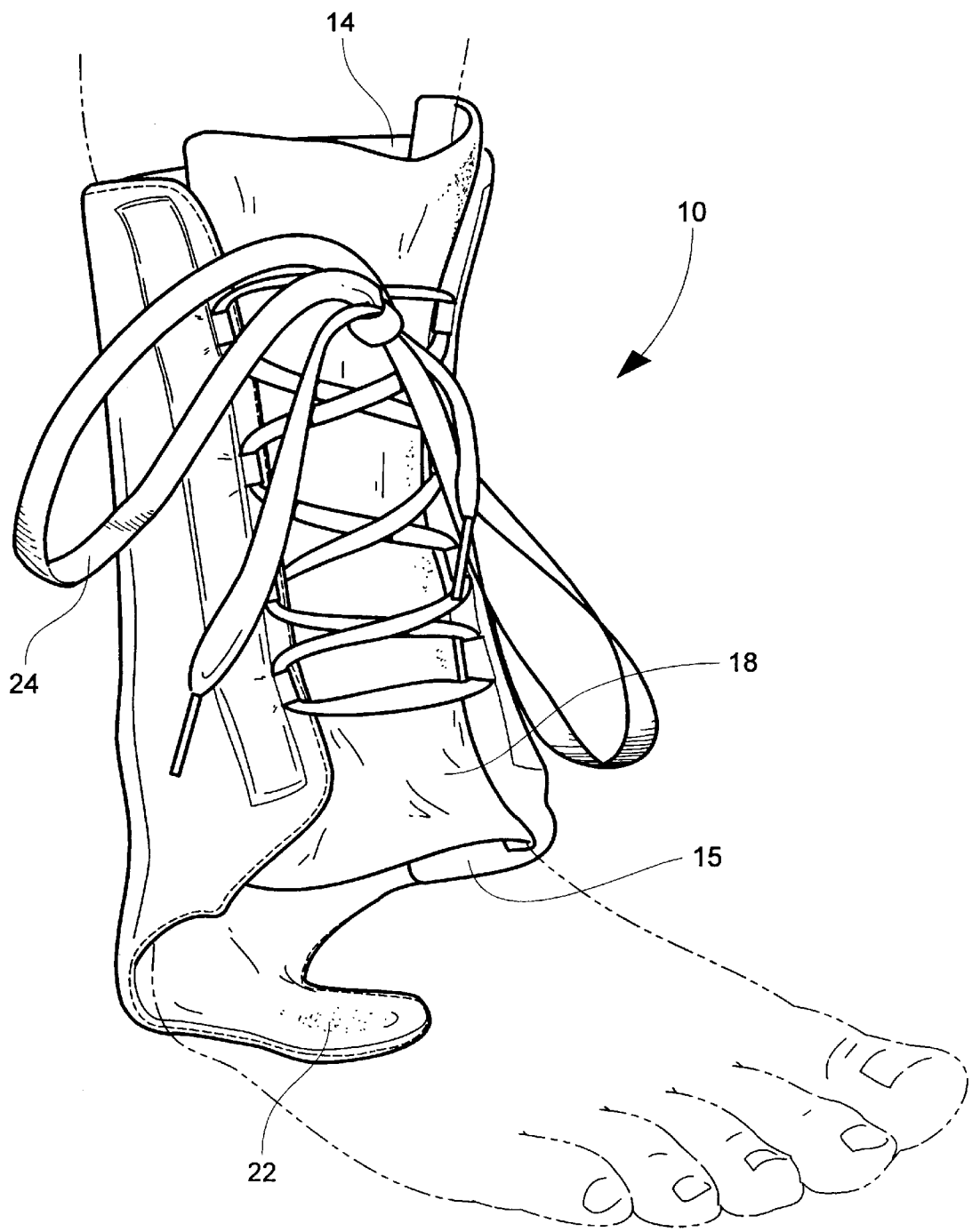
FIG. 1 is a perspective view of a custom-fitted ankle brace according to one preferred embodiment of the invention, and showing the brace applied to the wearer's lower leg shown in phantom.

Referring now specifically to the drawings, a custom-fitted ankle brace according to the present invention is illustrated in FIG. 1 and shown generally at reference numeral 10. The ankle brace 10 is preferably formed of a hardenable brace panel 11, shown in FIG. 6, which is packaged in a substantially flat, flexible condition and stored prior to use in a sealed moisture-impervious foil (not shown). After removing from the foil, the brace panel 11 is molded while flexible to the medial and lateral aspects of the lower leg and ankle of the wearer (See FIG. 1), and upon hardening, provides a rigid custom fit covering the medial and lateral prominences of the calcaneus and restricting inversion and eversion of the foot during wear.

The term "hardenable" is defined herein as transforming from a generally flexible condition to a semi-rigid or rigid condition, as in the case of products impregnated or coated with, for example, a thermosetting polymer resin or a moisture curable resin, such as described below.

Figure 2:
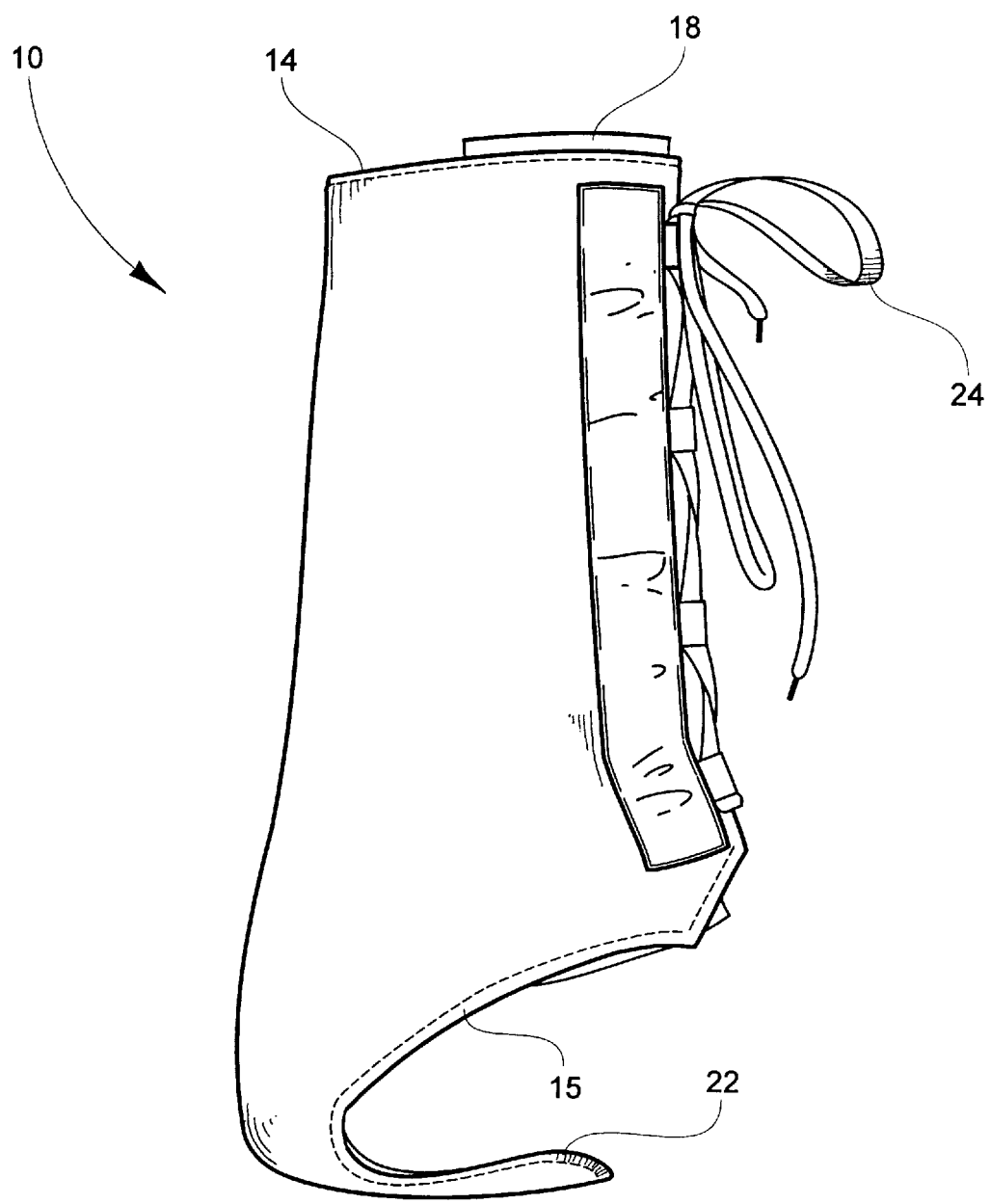
FIG. 2 is a side elevational view of the ankle brace.
Figure 3:
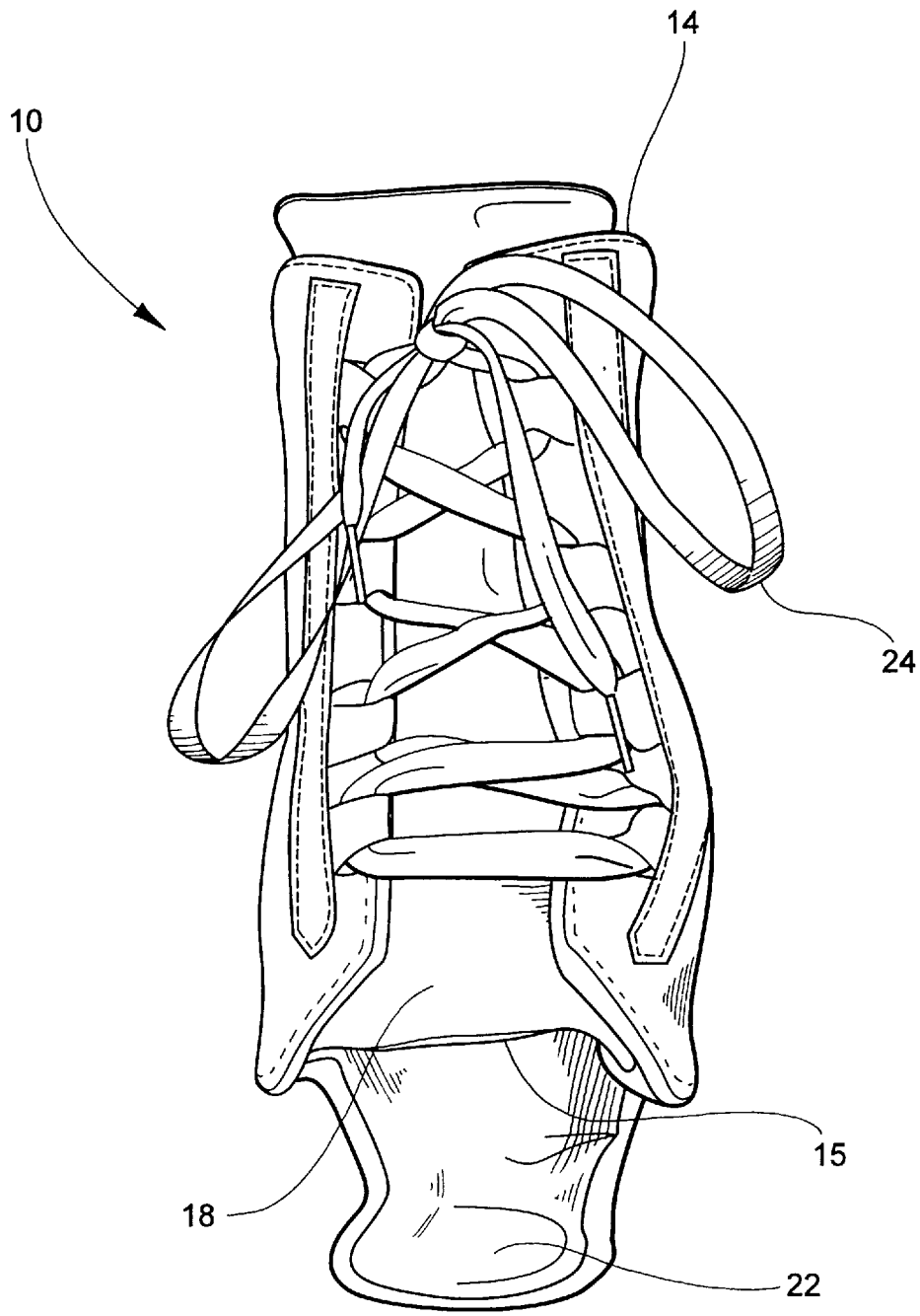
FIG. 3 is a front elevational view of the ankle brace.

Referring now to FIGS. 1–3, the ankle brace 10 includes respective openings 14 and 15 at its proximal and distal ends for receiving the foot of the wearer, and a separately attached anterior tongue 18 positioned to extend along the front of the lower leg from the proximal end to the distal end of the ankle brace 10. The tongue 18 is preferably formed of a soft flexible cushioning material such as 5.3 oz. polypropylene felt. An integrally-formed posterior heel tongue 22 extends forwardly from the distal end of the ankle brace 10 a spaced-apart distance from the opening 15 to reside under the heel of the wearer. The tongue 22 is hardenable, and is molded while flexible to the bottom of the heel to further customize the ankle brace 10 to the particular wearer. The heel tongue 22 has sufficient flex to allow generally normal dorsiflexion and planoflexion of the foot such as when walking or running.

Figure 4:
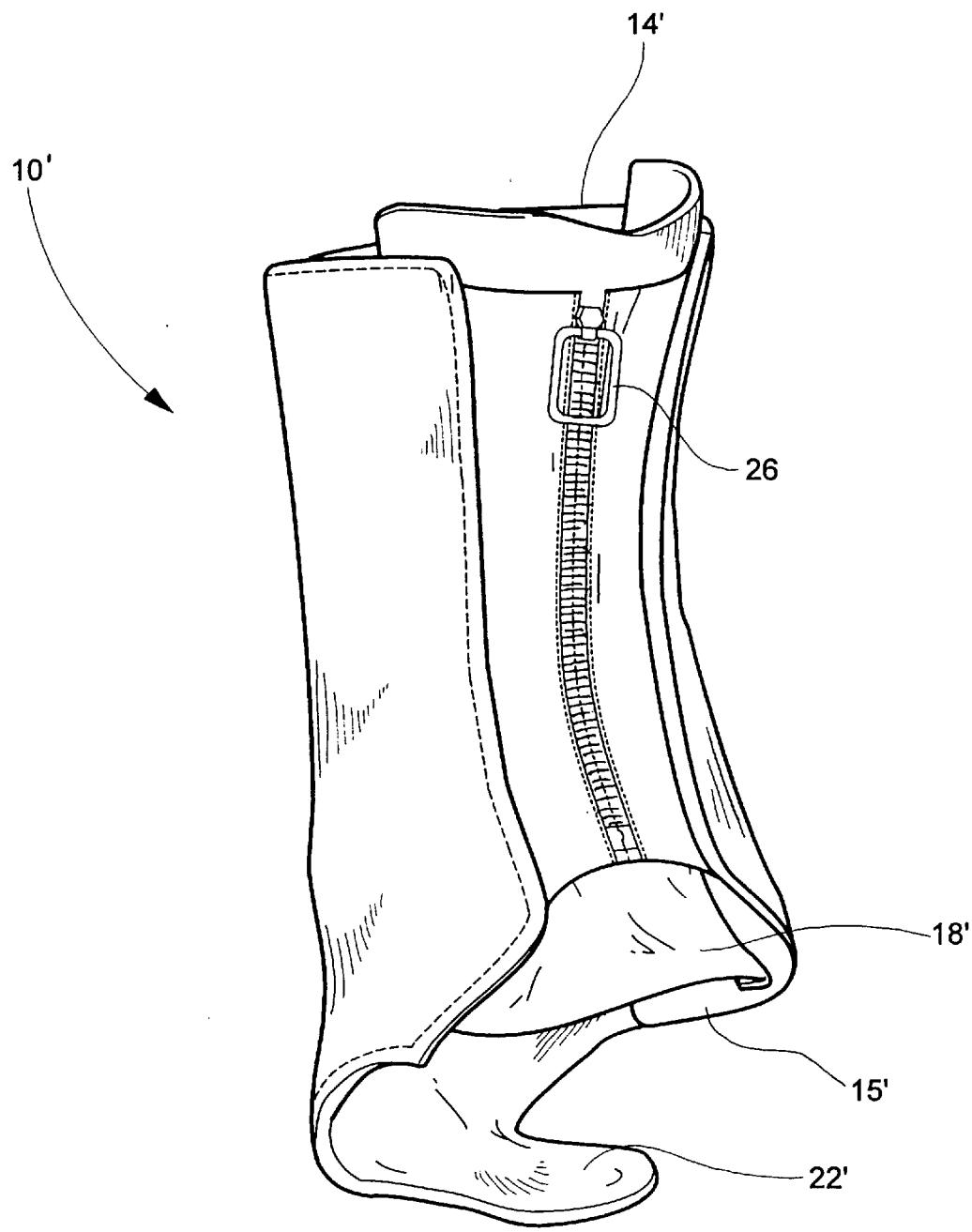
FIG. 4 is a perspective view of the ankle brace showing an alternative fastening means for securing the brace to the ankle.
Figure 5:
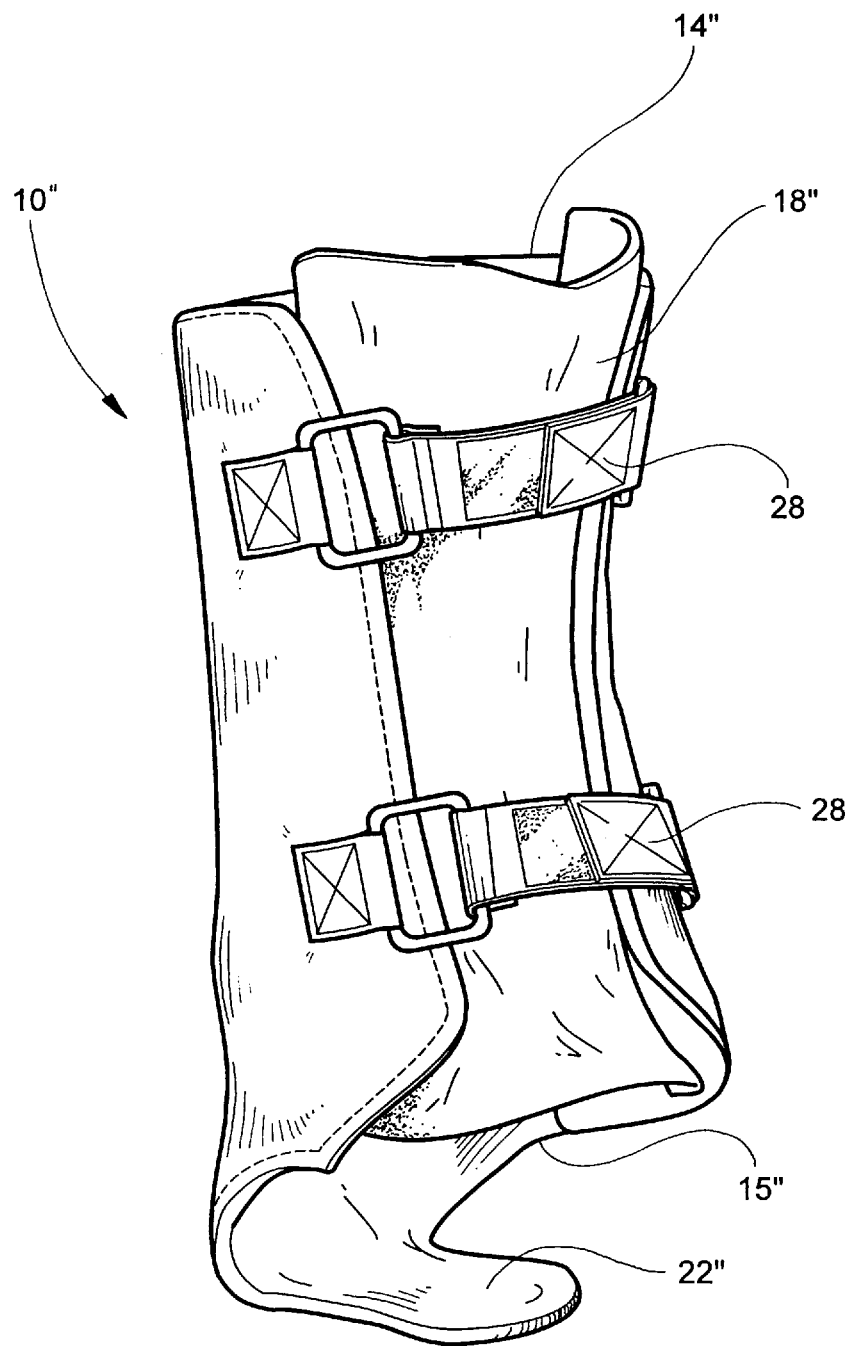
FIG. 5 is a perspective view of the ankle brace showing a further alternative fastening means for securing the brace to the ankle.

Fastening means, such as cooperating laces 24, are preferably attached to opposing anterior edges of the molded brace panel 11 and extend over the cushioning tongue 18 to secure and maintain the ankle brace 10 in position during wear. Alternative fastening means are illustrated in FIGS. 4 and 5. Like elements are shown in prime and double prime notation, respectively. The ankle brace of FIG. 4 includes a zipper fastener 26, while the ankle brace of FIG. 5 uses mating hook and loop straps 28.

Figure 6:
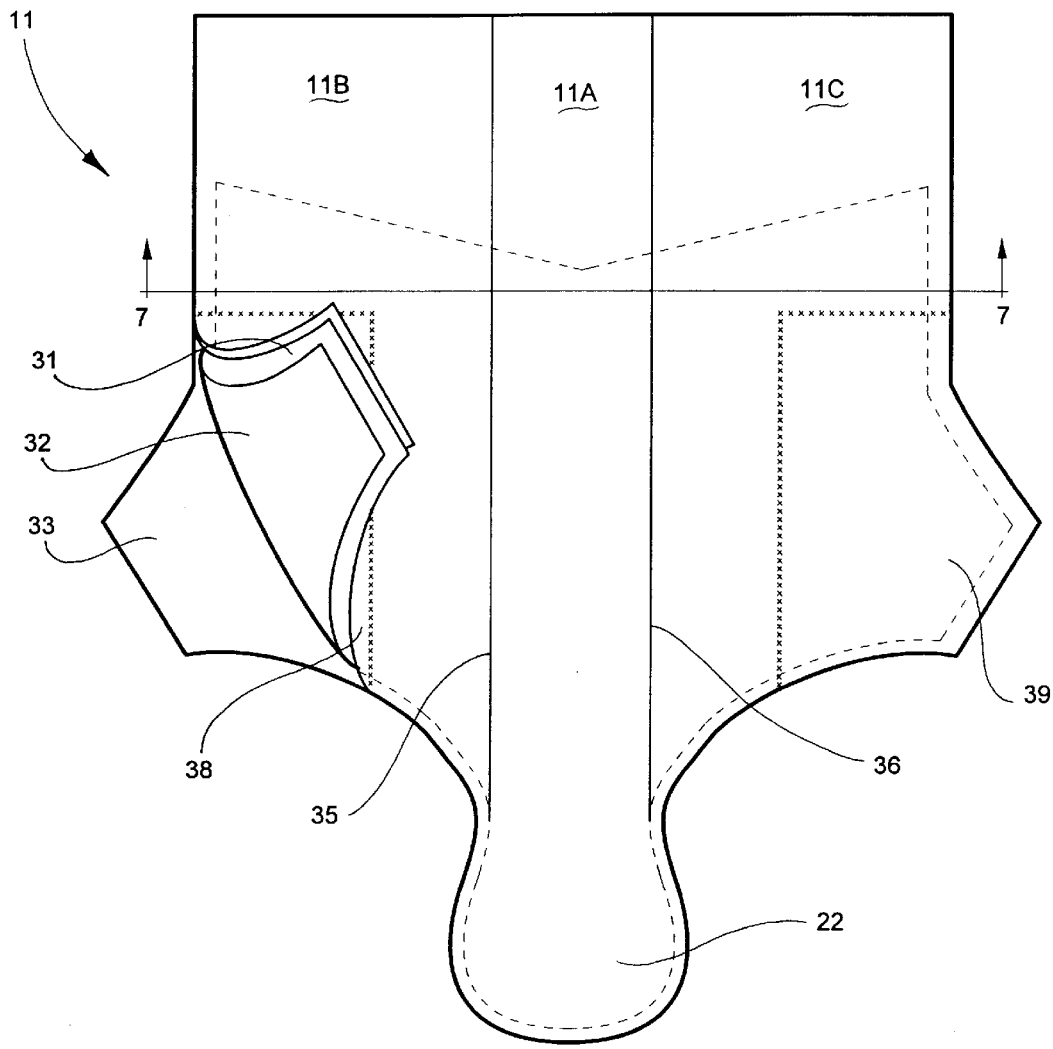
FIG. 6 is a plan view of the brace panel prior to being molded to the ankle of the wearer.
Figure 7:
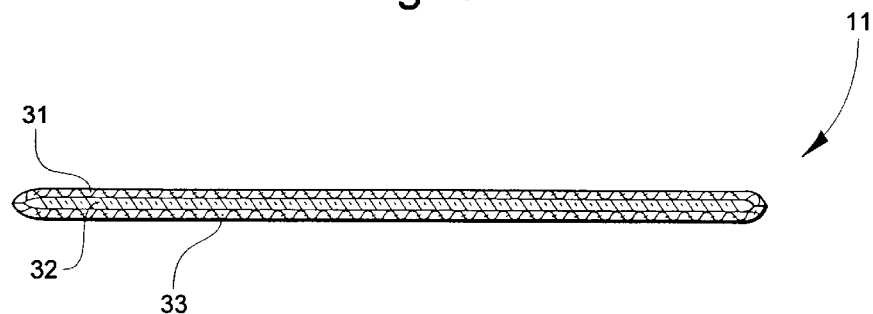
FIG. 7 is a cross-sectional view taken substantially along lines 7—7 of FIG. 6.

The material construction of the brace panel 11 is illustrated in FIGS. 6 and 7. As shown, the brace panel 11 has an inner layer 31 for residing next to the skin of the wearer, an intermediate layer 32 overlying a substantial portion of the inner layer 31, and an outer layer 33. The inner layer 31 is formed of a soft cushioning fabric, such as 5.3 oz. polypropylene felt. The polypropylene fabric, being hydrophobic, promotes dryness next to the skin and therefore discourages itching, rashes and infection. The outer layer 33 is formed of a performance fabric, such as polyester, and is sewn with, for example, a serging seam directly to the edges of the inner layer 31 to enclose the intermediate layer 32 therebetween. One preferred outer layer fabric is a polyester netting manufactured by Faytex Corporation of Weymouth, Mass., and sold under the trademark DRI-LEX.

The intermediate layer 32 is preferably formed of a single layer of fiberglass fabric impregnated or coated with a moisture-curable resin such as polyisocyanate as described in full in the present applicant's U.S. Pat. No. 4,770,299. This reactive system remains stable when maintained in substantially moisture-free conditions, such as in the moisture-impervious foil mentioned above, but hardens upon exposure to sufficient moisture to form a rigid, self-supporting structure. A typical formulation of the reactive system is set forth in the following table:

| Typical Formulation: | | | |
|---|---|---|---|
| Isonate↓ 143L | or | | |
| Mondur↓ CD | or | polyisocyanate | 50.0% |
| Rubinate↓ XI168 | | | |
| Pluracol↓ P1010 | | polyol | 46.6% |
| DC-200 Silicone | | defoaming agent | 0.30% |
| Benzoyl Chloride | | stabilizer | 0.10% |
| Thancat↓ DM-70 | | catalyst | |
| | | | 100% |

A complete discussion of the parameters of the reactive system, the manner of production and the variables which apply are found in U.S. Pat. No. 4,411,262. The entire disclosure of this patent is incorporated herein by reference.

The polyisocyanate resin remains in a viscous, liquid unhardened state so long as the resin is not exposed to moisture. This permits the fiberglass layer to remain flexible and moldable so long as the resin is not exposed to moisture, and for a relatively short period of time after exposure to moisture. The curing time can be controlled to some extent by the quantity of water to which the resin is exposed. For example, exposure to water by dipping will result in quite rapid curing, while merely allowing the resin to be exposed to air will cause long curing times proportional to the amount of moisture in the air to which it is exposed.

According to one preferred fitting technique, the brace panel 11 is first applied while flexible to the lower leg and ankle of the wearer and is then wrapped using an absorbent fitting wrap, such as an ACE bandage. The ankle brace 10 is then dipped in a water bath to fully saturate the resin-impregnated fiberglass layer, thereby causing the brace panel 11 to harden in the shape of the lower leg and ankle to provide a custom fit. The top of the brace panel 11 above the fiberglass layer remains soft and flexible for added comfort. According to an alternative technique, the brace panel 11 is applied while flexible to the lower leg and ankle of the wearer and is then wrapped with a wetted fitting wrap to cause hardening.

To allow sufficient flex for inserting and removing the foot into and from the ankle brace 10 after hardening, the brace panel 11 further includes a pair of longitudinally extending hinge lines 35 and 36 formed by sewing stitches passing entirely through the brace panel 11 from one side to the other. The hinge lines 35 and 36 define a center brace segment 11A and two outer brace segments 11B and 11C. The outer brace segments 11B and 11C are flexible at respective hinge lines 35 and 36 to adjust the fit of the ankle brace 10 as desired.

In addition, for added comfort, the ankle brace 10 may include pressure relief ankle bone pads 38 and 39 sewn to the inner layer 31 of the brace panel 11 and positioned to reside against the medial and lateral prominences of the calcaneus after the brace panel 11 is molded around the ankle. The ankle bone pads 38 and 39 include a gel core covered by a performance fabric. An example of one preferred pad is that manufactured by Silipos of Niagara Falls, N.Y., and sold under the trademark SILIPOS. A separately molded heel cup (not shown) may also be provided in the heel of the ankle brace 10 for added support.

The embodiment of the invention described above and shown in FIGS. 1–7 is especially suited for athletic use. The intermediate fiberglass layer 32 completely covers and protects the Achilles tendon of the wearer while allowing a substantial range of motion the foot. The ankle brace 10 is sufficiently thin to fit comfortable inside the shoe of the wearer.

An alternative embodiment of an ankle brace 50 is shown in FIGS. 8–11 and described below. Like the ankle brace 10, the ankle brace 50 is formed of a hardenable brace panel 51, shown in FIG. 9, which is packaged in a substantially flat, flexible condition and stored prior to use in a sealed moisture-impervious foil (not shown).

Figure 8:
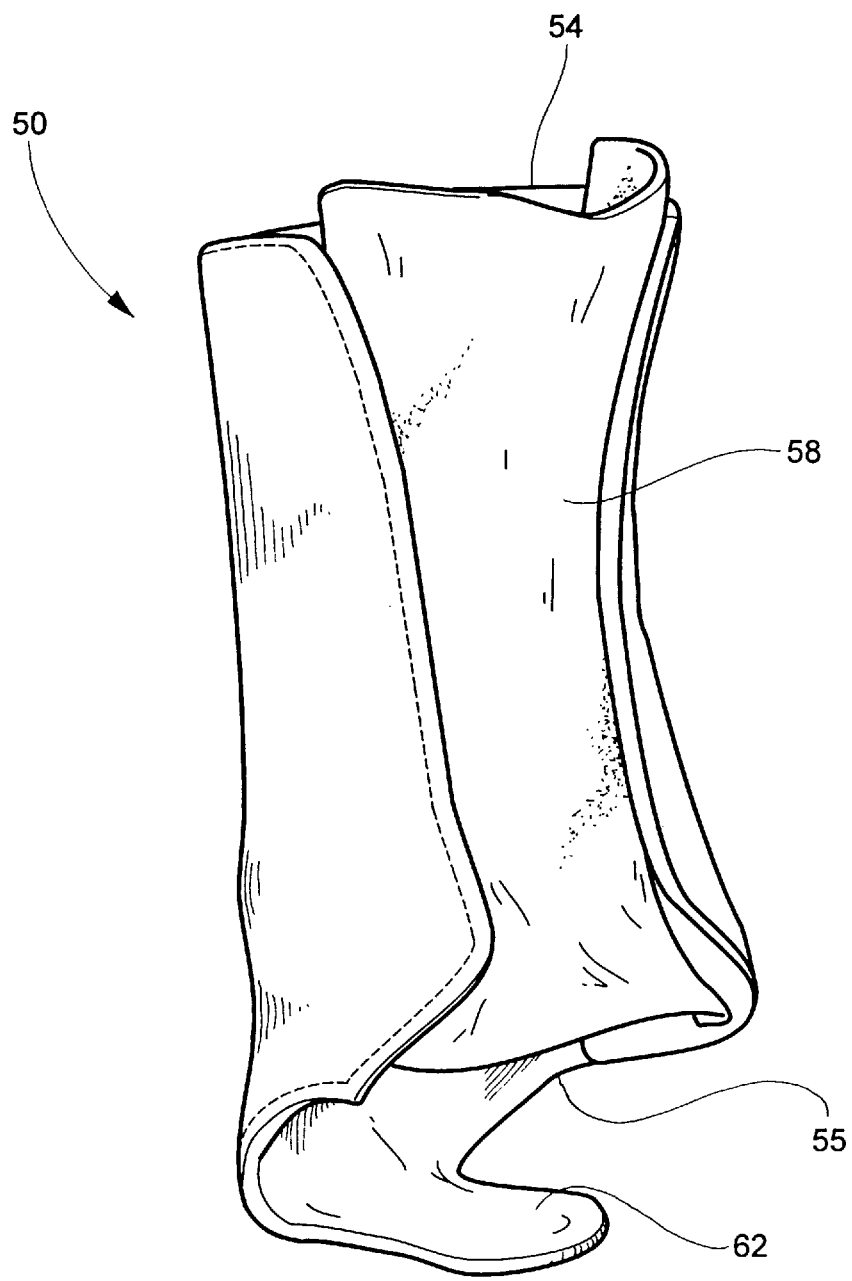
FIG. 8 is a perspective view of the ankle brace according to an alternative embodiment of the invention.

Referring to FIG. 8, the ankle brace 50 includes respective openings 54 and 55 at its proximal and distal ends for receiving the foot of the wearer, and a separately attached anterior tongue 58 positioned to extend along the front of the lower leg from the proximal end to the distal end of the ankle brace 50. The tongue 58 is preferably formed of a soft flexible cushioning material such as 5.3 oz. polypropylene felt. An integrally-formed posterior heel tongue 62 extends forwardly from the distal end of the ankle brace 50 a spaced-apart distance from the opening 55 to reside under the heel of the wearer. The tongue 62 is hardenable, and is molded while flexible to the bottom of the heel to further customize the ankle brace 50 to the particular wearer.

The ankle brace 50 of this embodiment may or may not include fastening means. One suitable fastening means, however, includes an outer wrapping, such as an ACE bandage (not shown).

Figure 9:
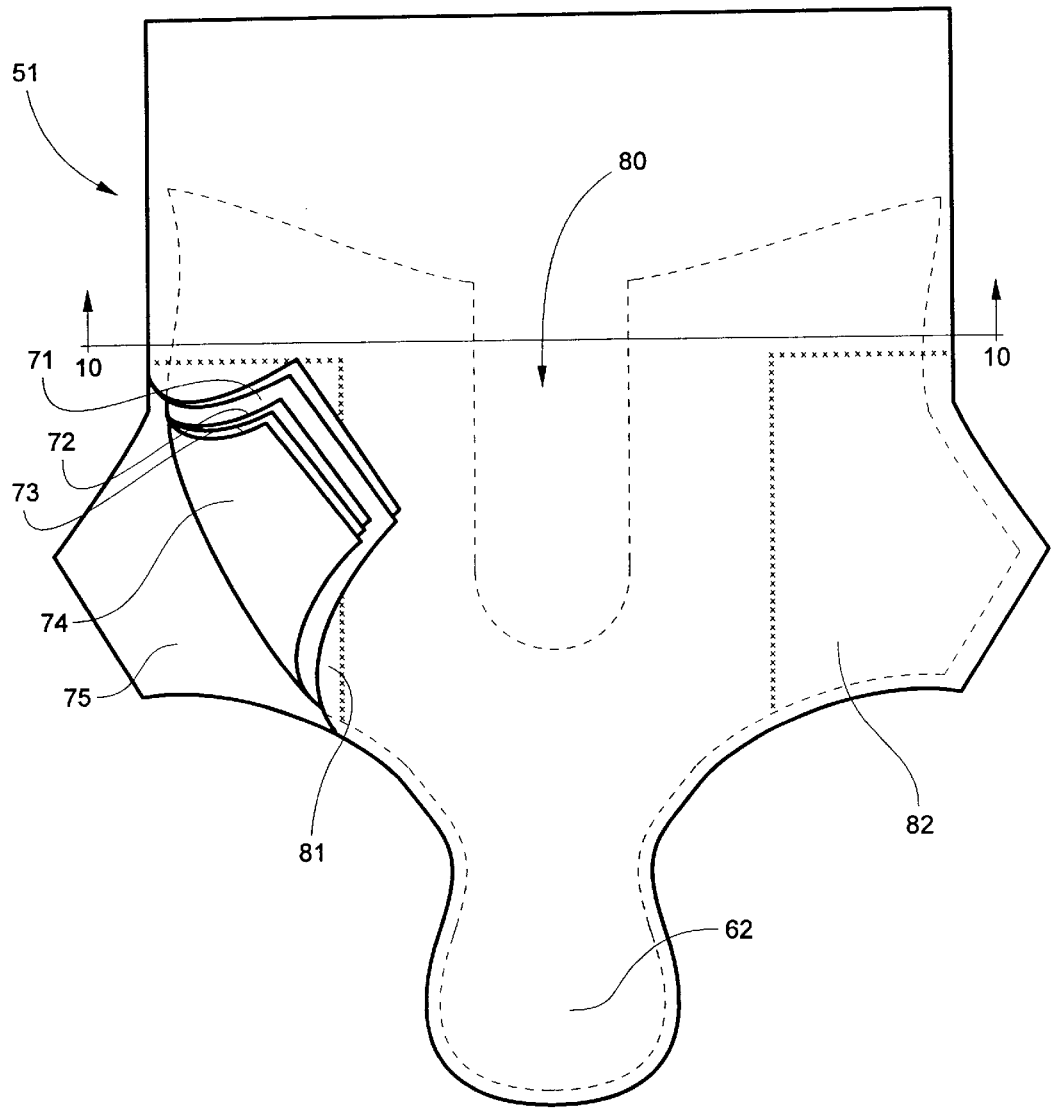
FIG. 9 is a plan view of the alternative brace panel prior to being molded to the ankle of the wearer.
Figure 10:
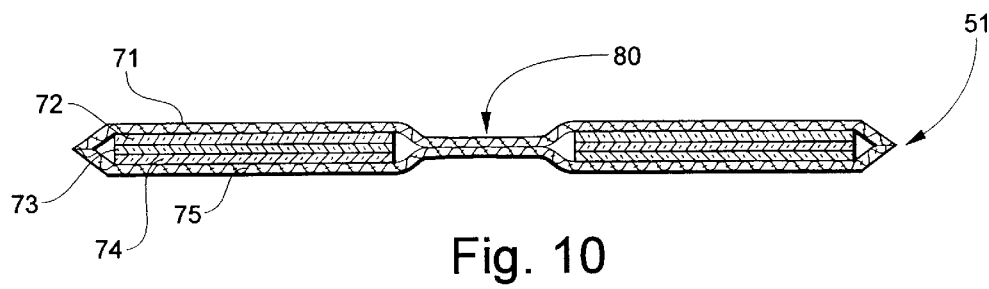
FIG. 10 is a cross-sectional view taken substantially along lines 10—10 of FIG. 9.

The material construction of the brace panel 51 is illustrated in FIGS. 9 and 10. As shown, the brace panel 51 has an inner layer 71 for residing next to the skin of the wearer, several overlying intermediate layers 72, 73, and 74 covering a portion of the inner layer 71, and an outer layer 75. The inner layer 71 is formed of a soft cushioning fabric, as 5.3 oz. polypropylene felt. The polypropylene fabric, being hydrophobic, promotes dryness next to the skin and therefore discourages itching, rashes and infection. The outer layer 75 is formed of a performance fabric, such as polyester, and is sewn with, for example, a serging seam directly to the edges of the inner layer 71 to enclose the intermediate layers 72, 73, and 74 therebetween. One preferred outer layer fabric is a polyester netting manufactured by Faytex Corporation of Weymouth, Mass., and sold under the trademark DRI-LEX.

The intermediate layers 72, 73, and 74 are preferably formed of fiberglass fabric impregnated or coated with a moisture-curable resin such as polyisocyanate, as described above. The fiberglass fabric layers 72, 73, and 74 may also be covered with a foam protective pad (not shown), which may be a single thickness or a laminated structure. One preferred embodiment is a ⅜ inch, six pound EVA (ethylene vinyl acetate) pad. Another embodiment may be a ⅜ inch laminated pad of a ⅛ inch outer EVA pad and a ¼ inch outer polyethylene/polyurethane, combination open and closed cell foam. The pad provides cushioning between the skin and the rigid fiberglass layers 72, 73, and 74. The foam layer is flexible enough to bend easily with the other components of the ankle brace 50 during fitting and curing. The pad extends the entire length of the ankle brace 50 including the area of the heel tongue 62.

Figure 11:
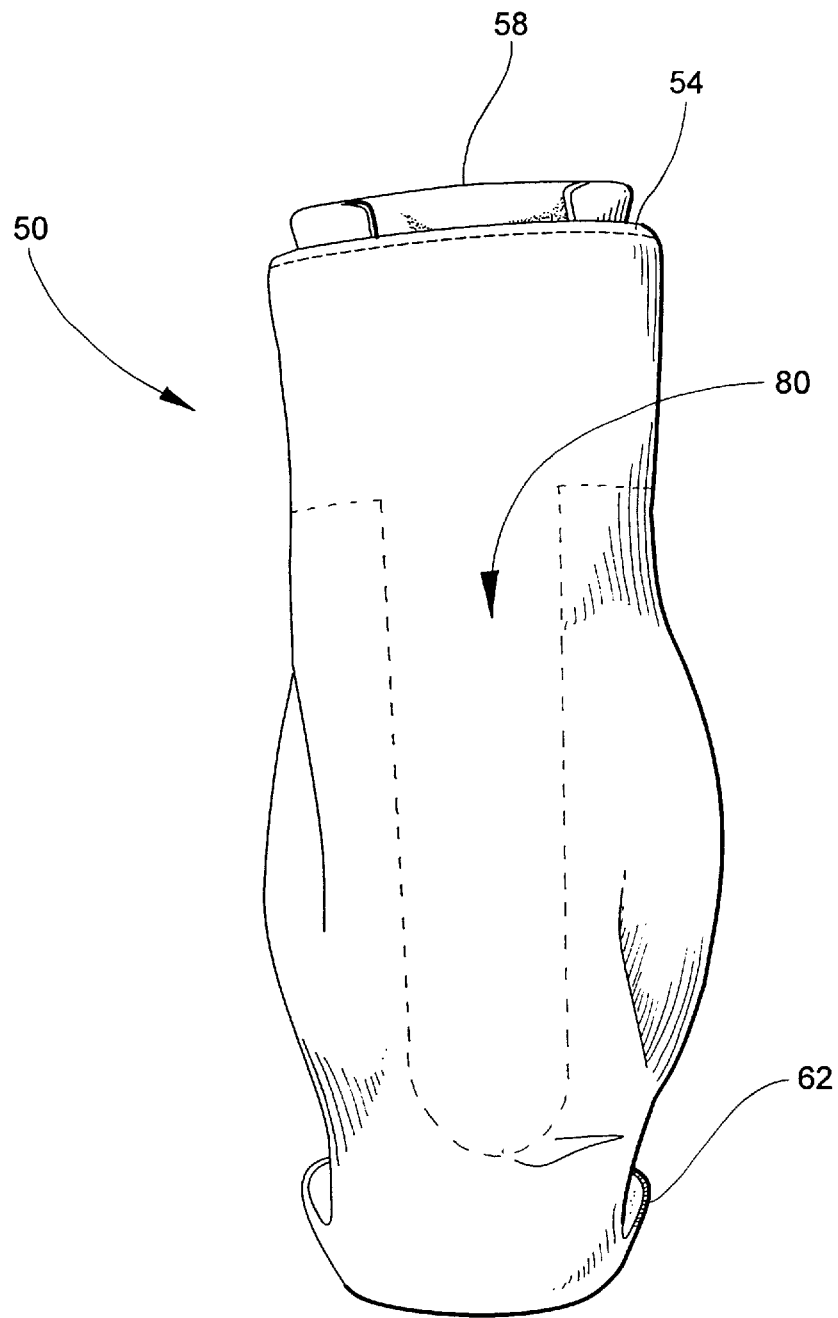
FIG. 11 is a rear elevational view of the ankle brace according to the alternative embodiment.

As shown in FIGS. 9 and 11, the fiberglass layers 72, 73, and 74 are arranged in registration to define an Achilles zone 80 of increased flexibility which extends along a vertical dimension of the Achilles tendon of the wearer upon application of the brace panel to the ankle. The Achilles zone 80 is preferably completely devoid of hardenable fiberglass fabric in order to allow flexing of the Achilles tendon upon dorsiflexion and planoflexion of the foot. This increases the overall comfort of the ankle brace 50 while providing ample support to the ankle. Alternatively, the Achilles zone 80 may include a lesser number of fiberglass fabric layers, thus forming a semi-rigid area having sufficient flexibility to allow flexing of the Achilles tendon. The ankle brace 50 is preferably applied to the wearer using the fitting techniques described above.

In addition, for added comfort, the ankle brace 50 may include pressure relief ankle bone pads 81 and 82 sewn to the inner layer 71 of the brace panel 51 and positioned to reside against the medial and lateral prominences of the calcaneus after the brace panel 51 is molded around the ankle. The ankle bone pads 81 and 82 include a gel core covered by a performance fabric, as described above. A separately molded heel cup (not shown) may also be provided in the heel of the ankle brace 50 for added support.

According to a further alternative embodiment, the ankle brace includes a brace panel made of a thermosetting material which is formed while flexible to the lower leg and ankle of the wearer and permanently set to provide a rigid custom fit. The panel may further include one or more cushioning layers covering the thermosetting material for added comfort.

A custom fitted ankle brace is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

We claim:

1. An ankle brace for being custom-formed to the shape of a wearer's ankle, said ankle brace comprising:

(a) a brace panel adapted for being formed to the medial, dorsal, and lateral aspects of the lower leg and ankle of the wearer, and permanently molded to provide a rigid custom fit for restricting inversion and eversion of the foot during wear; and (b) a posterior heel tongue integrally-formed as an extension of said brace panel and sized sufficiently for extending downwardly along the dorsal aspect of the lower leg and under and along the calcaneus portion of the heel for being formed to the heel of the wearer and permanently molded to further support the ankle.

2. An ankle brace according to claim 1, wherein said brace panel defines a flexible Achilles zone adapted for extending along a vertical dimension of the Achilles tendon of the wearer to allow flexing of the Achilles tendon upon dorsiflexion and planoflexion of the foot.

3. An ankle brace according to claim 2, wherein said brace panel comprises a plurality of fiberglass fabric layers impregnated with a moisture-curable resin which hardens when exposed to moisture.

4. An ankle brace according to claim 3, wherein the Achilles zone of said brace panel is completely devoid of fiberglass fabric.

5. An ankle brace according to claim 1, and comprising fastener means for securing the brace panel in position around the lower leg and ankle of the wearer.

6. An ankle brace according to claim 5, wherein said fastener means comprises a zipper extending from a proximal end of the ankle brace to a distal end of the ankle brace.

7. An ankle brace according to claim 5, wherein said fastener means comprises complementary hook and loop straps.

8. An ankle brace according to claim 5, wherein said fastener means comprises cooperating laces.

9. An ankle brace according to claim 1, and comprising at least one longitudinal hinge line dividing said brace panel into adjacent brace segments flexibly attached together along said hinge line, and cooperating to allow ready insertion and removal of the foot into and from the ankle brace.

10. An ankle brace according to claim 9, wherein said hinge line comprises sewing stitches.

11. An ankle brace according to claim 1, and comprising a cushioned anterior tongue adapted for residing adjacent to a front portion of the lower leg and ankle.

12. An ankle brace according to claim 1, wherein said brace panel comprises a single layer of fiberglass fabric impregnated with a moisture-curable resin which hardens when exposed to moisture.

13. An ankle brace according to claim 1, wherein said brace panel comprises an inner cushioning layer for residing next to the skin.

14. An ankle brace according to claim 13, wherein said inner cushioning layer comprises polypropylene felt.

15. An ankle brace according to claim 1, wherein said brace panel comprises an outer layer formed of polyester netting.

* * * * *